United States Patent
Horie

(10) Patent No.: US 11,910,993 B2
(45) Date of Patent: Feb. 27, 2024

(54) ENDOSCOPIC TASK SUPPORTING SYSTEM AND ENDOSCOPIC TASK SUPPORTING METHOD FOR EXTRACTING ENDOSCOPIC IMAGES FROM A PLURALITY OF ENDOSCOPIC IMAGES BASED ON AN AMOUNT OF MANIPULATION OF A TIP OF AN ENDOSCOPE

(71) Applicant: OLYMPUS CORPORATION, Tokyo (JP)

(72) Inventor: Gen Horie, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 773 days.

(21) Appl. No.: 17/065,096

(22) Filed: Oct. 7, 2020

(65) Prior Publication Data

US 2021/0015340 A1  Jan. 21, 2021

Related U.S. Application Data

(63) Continuation of application No. PCT/JP2018/014921, filed on Apr. 9, 2018.

(51) Int. Cl.
  *A61B 1/00* (2006.01)
  *A61B 1/045* (2006.01)
  *A61B 1/005* (2006.01)

(52) U.S. Cl.
  CPC ........ *A61B 1/00006* (2013.01); *A61B 1/0004* (2022.02); *A61B 1/0005* (2013.01);
  (Continued)

(58) Field of Classification Search
  None
  See application file for complete search history.

(56) References Cited

U.S. PATENT DOCUMENTS

| 5,432,543 A | 7/1995 | Hasegawa et al. |
| 2005/0002547 A1* | 1/2005 | Torre-Bueno ......... G06T 7/0012 |
| | | 375/E7.137 |

(Continued)

FOREIGN PATENT DOCUMENTS

| CN | 101347355 A | 1/2009 |
| CN | 101849843 A | 10/2010 |

(Continued)

OTHER PUBLICATIONS

International Search Report dated Jun. 26, 2018 issued in International Application No. PCT/JP2018/014921.

(Continued)

*Primary Examiner* — John P Leubecker
(74) *Attorney, Agent, or Firm* — Scully, Scott, Murphy &n Presser, P.C.

(57) ABSTRACT

An endoscopic task supporting system including: an image storage that stores a plurality of endoscopic images acquired in a time series; a three-dimensional data generation unit that generates three-dimensional data indicating a three-dimensional shape of a predetermined part subject to observation, based on the plurality of endoscopic images stored in the image storage; a two-dimensional image generation unit that generates, from the three-dimensional data generated by the three-dimensional data generation unit, a two-dimensional image corresponding to a viewpoint position and a direction of line of sight entered; and a display control unit that causes a predetermined display unit to display the two-dimensional image generated by the two-dimensional image generation unit.

5 Claims, 8 Drawing Sheets

(52) U.S. Cl.
CPC .......... *A61B 1/009* (2022.02); *A61B 1/00009* (2013.01); *A61B 1/00042* (2022.02); *A61B 1/00194* (2022.02); *A61B 1/045* (2013.01)

(56) References Cited

U.S. PATENT DOCUMENTS

| | | | | |
|---|---|---|---|---|
| 2005/0151730 | A1* | 7/2005 | Lobregt | G09B 23/285 |
| | | | | 348/E13.022 |
| 2007/0154075 | A1* | 7/2007 | Matsumoto | G06T 15/08 |
| | | | | 382/128 |
| 2007/0247454 | A1* | 10/2007 | Rahn | A61B 6/5235 |
| | | | | 345/419 |
| 2009/0074265 | A1* | 3/2009 | Huang | G16H 30/40 |
| | | | | 382/128 |
| 2009/0208143 | A1* | 8/2009 | Yoon | A61B 5/065 |
| | | | | 382/312 |
| 2009/0259102 | A1* | 10/2009 | Koninckx | A61B 1/00194 |
| | | | | 348/E13.001 |
| 2013/0018255 | A1 | 1/2013 | Kitamura et al. | |
| 2015/0087981 | A1* | 3/2015 | Ishii | G01S 7/52065 |
| | | | | 600/443 |
| 2015/0208904 | A1* | 7/2015 | Yoon | A61B 1/0005 |
| | | | | 600/102 |
| 2016/0292498 | A1 | 10/2016 | Miura | |
| 2018/0368656 | A1* | 12/2018 | Austin | A61B 1/045 |

FOREIGN PATENT DOCUMENTS

| | | | |
|---|---|---|---|
| CN | 102821670 | A | 12/2012 |
| CN | 103561628 | A | 2/2014 |
| JP | 1992049939 | A | 2/1992 |
| JP | 1992261637 | A | 9/1992 |
| JP | 1994007289 | A | 1/1994 |
| JP | 2016007444 | A | 1/2016 |
| JP | 2016062488 | A | 4/2016 |
| JP | 2016-189812 | A | 11/2016 |
| WO | WO-9800811 | A1 * | 1/1998 ............ G06F 15/00 |
| WO | 2014/141968 | A1 | 9/2014 |

OTHER PUBLICATIONS

English translation of International Preliminary Report on Patentability dated Oct. 13, 2020, together with the Written Opinion issued in International Application No. PCT/JP2018/014921.

Japanese Office Action dated May 31, 2022 received in 2020-512952.

Chinese Office Action dated Nov. 5, 2021 received in 201880092198.7.

* cited by examiner

FIG.3

| EXAMINATION ID | PATIENT ID | EXAMINATION DATE | IMAGE ID |
|---|---|---|---|
| 1 | cc | 2018/1/10 | 1〜1000 |
| 2 | dd | 2018/1/10 | 1001〜2005 |
| 3 | ee | 2018/1/10 | 2006〜2989 |
| 4 | ff | 2018/1/10 | 2990〜4100 |
| 5 | cc | 2018/1/12 | 4101〜6003 |
| 6 | gg | 2018/1/12 | 6004〜7005 |
| 7 | hh | 2018/1/12 | 7006〜8400 |

FIG.5

| LIST OF EXAMINATION INFORMATION SCREEN | | |
|---|---|---|
| EXAMINATION ID | PATIENT ID | EXAMINATION DATE |
| 1 | cc | 2018/1/10 |
| 2 | dd | 2018/1/10 |
| 3 | ee | 2018/1/10 |
| 4 | ff | 2018/1/10 |
| 5 | cc | 2018/1/12 |
| 6 | gg | 2018/1/12 |
| 7 | hh | 2018/1/12 |

OK  CANCEL

ENDOSCOPIC TASK SUPPORTING SYSTEM AND ENDOSCOPIC TASK SUPPORTING METHOD FOR EXTRACTING ENDOSCOPIC IMAGES FROM A PLURALITY OF ENDOSCOPIC IMAGES BASED ON AN AMOUNT OF MANIPULATION OF A TIP OF AN ENDOSCOPE

CROSS-REFERENCE TO RELATED APPLICATIONS

This application is based upon and claims the benefit of priority from International Application No. PCT/JP2018/014921, filed on Apr. 9, 2018, the entire contents of which is incorporated herein by reference.

BACKGROUND OF THE INVENTION

1. Field of the Invention

The present invention relates to a technology of supporting endoscopic tasks.

2. Description of the Related Art

In an endoscopic examination, an endoscopic image acquired by an endoscope inserted into the body of a patient is displayed on a display apparatus in real time. A doctor makes an observation by viewing the image displayed on the display apparatus. Further, a plurality of endoscopic images are normally recorded in an endoscopic examination.
[Patent literature 1] JP2016-062488

In some cases, endoscopic images recorded in an examination are used for a diagnosis of the patient. For example, the images may be used in a diagnosis for a second opinion. The doctor making a diagnosis often views concavities and convexities on the biological surface. In making a diagnosis using an endoscopic image, the doctor may desire to view an endoscopic image taken in a position and a direction different from those of the endoscopic image prepared in order to understand concavities and convexities on the biological surface more accurately.

Such an issue arises not only in the case of diagnosing a patient by referring to an endoscopic image capturing the inside of the patient's body but also in the case of diagnosing other targets subject to observation by referring to an image capturing the targets subject to observation (e.g., in the case of diagnosing a pipe, a machine, a structure, etc. by referring to an image capturing the inside of the pipe, the machine, the structure, etc.).

SUMMARY OF THE INVENTION

The present invention addresses the above-described issue, and a general purpose thereof is to provide a technology capable of diagnosing a target subject to observation more accurately by using an endoscopic image.

An image processing system according to an embodiment of the present invention includes: an image storage that stores a plurality of endoscopic images acquired in a chronological order; a three-dimensional data generation unit that generates three-dimensional data indicating a three-dimensional shape of a predetermined part subject to observation, based on the plurality of endoscopic images stored in the image storage; a two-dimensional image generation unit that generates, from the three-dimensional data generated by the three-dimensional data generation unit, a two-dimensional image corresponding to a viewpoint position and a direction of line of sight entered; and a display control unit that causes a predetermined display unit to display the two-dimensional image generated by the two-dimensional image generation unit.

Another embodiment of the present invention relates to an image processing method. The method is for execution by an image processing system capable of accessing a predetermined storage area that stores a plurality of endoscopic images acquired in a chronological order and includes: generating three-dimensional data indicating a three-dimensional shape of a predetermined part inside a body, based on the plurality of endoscopic images stored in the storage area; generating, from the three-dimensional data generated, a two-dimensional image corresponding to a viewpoint position and a direction of line of sight entered; and causing a predetermined display unit to display the two-dimensional image generated.

Optional combinations of the aforementioned constituting elements, and implementations of the invention in the form of methods, apparatuses, systems, recording mediums, and computer programs may also be practiced as additional modes of the present invention.

BRIEF DESCRIPTION OF THE DRAWINGS

Embodiments will now be described by way of examples only, with reference to the accompanying drawings which are meant to be exemplary, not limiting and wherein like elements are numbered alike in several Figures in which:

FIG. 3 shows a data structure in the examination information storage of FIG. 2;

FIG. 5 shows an example of a list of examination information;

DETAILED DESCRIPTION OF THE INVENTION

Figure 1:
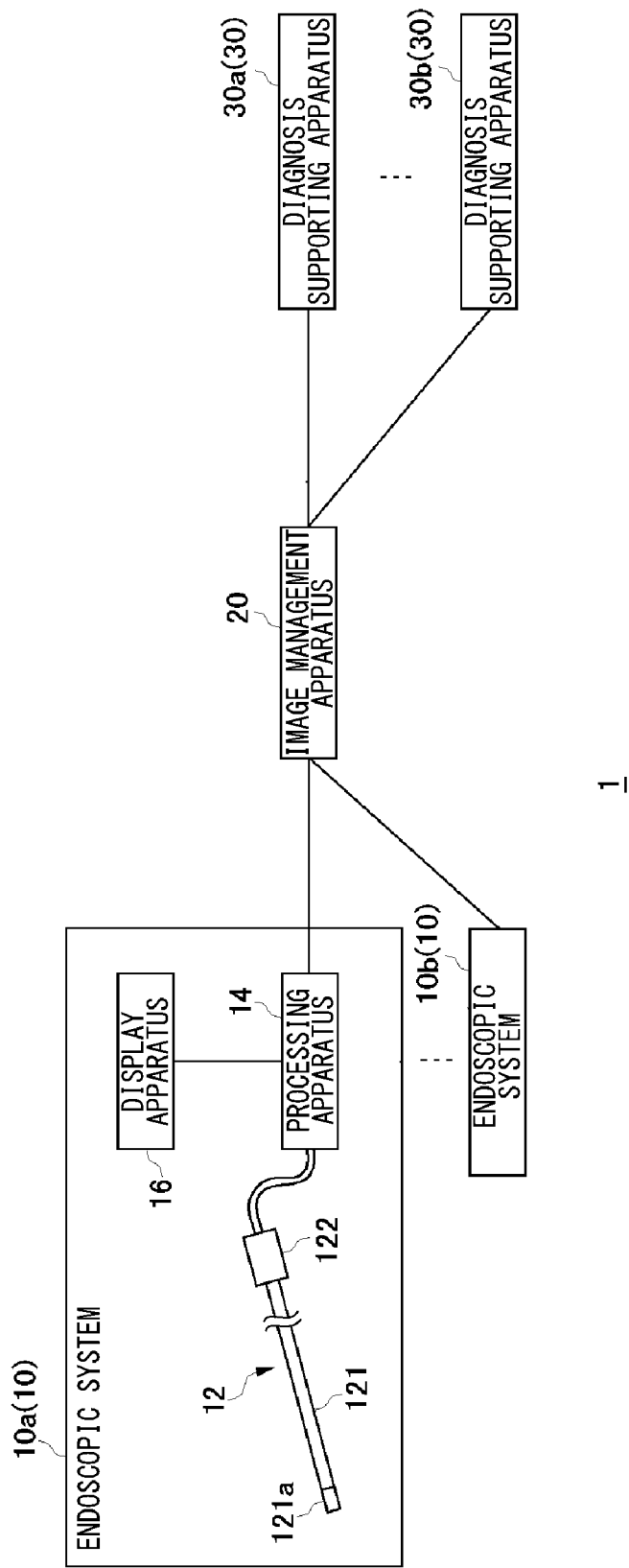
FIG. 1 shows a configuration of an endoscopic task supporting system according to the first embodiment.

The invention will now be described by reference to the preferred embodiments. This does not intend to limit the scope of the present invention, but to exemplify the invention.

A detailed description will be given of embodiments of the present invention with reference to the drawings. In the explanations of the figures, the same elements shall be denoted by the same reference numerals, and duplicative explanations will be omitted appropriately.

First Embodiment

FIG. 1 shows a configuration of an endoscopic task supporting system 1 according to the embodiment. The endoscopic task supporting system 1 is a system for supporting endoscopic tasks and includes a plurality of endoscopic systems 10a, 10b, generically referred to as endoscopic systems 10, an image management apparatus 20, and a plurality of diagnosis supporting apparatuses 30a, 30b, generically referred to as diagnosis supporting apparatuses 30. The endoscopic systems 10 and the diagnosis supporting apparatuses 30 are connected to the image management apparatus 20 via a network. The diagnosis supporting apparatuses 30 may be provided at a location geographically distanced from the endoscopic systems 10. Similarly, the image management apparatus 20 may be provided at a location geographically distanced from the endoscopic systems 10 and/or the diagnosis supporting apparatuses 30.

The endoscopic system 10 includes an endoscope 12, a processing apparatus 14, and a display apparatus 16. The endoscope 12 includes an inserted part 121 and a user controller 122. An imaging device is provided in a tip part 121a located at the tip of the inserted part 121. The first doctor inserts the inserted part 121 of the endoscope 12 to the inside of the patient's body from, for example, the mouth or the nose. The imaging device provided in the tip part 121a captures an image inside the patient's body. The taken image (hereinafter, referred to as "endoscopic image") is output to the processing apparatus 14. The user controller 122 includes an examination start button pressed to start an examination, an examination end button pressed to end the examination, and an angle knob for changing the orientation of the tip part 121a, i.e., for bending the tip of the inserted part 121.

The processing apparatus 14 controls the entirety of the endoscopic system 10 in an integrated manner. One of the important roles of the processing apparatus 14 is to transmit a plurality of endoscopic images acquired by the endoscope 12 in a chronological order to the image management apparatus 20 and cause the database to store the images. Another important role is to cause the display apparatus 16 to display the image acquired by the endoscope 12 in real time.

Before starting an endoscopic examination (hereinafter, simply referred to as "examination"), the first doctor enters an examination ID, which is information for identifying the examination, and a patient ID, which is information for identifying the patient, in the processing apparatus 14 using a user interface such as a keyboard. The first doctor starts the examination by pressing the start button of the user controller 122 of the endoscope 12. The processing apparatus 14 transmits examination start information, including the examination ID, the patient ID, and the examination date, to the image management apparatus 20. The first doctor makes an observation by viewing the image displayed on the display apparatus 16 in real time, while manipulating the endoscope 12. The first doctor presses the end button to end the examination. The processing apparatus 14 transmits examination end information, including the examination ID, the patient ID, and the examination date, to the image management apparatus 20.

During the examination that begins when the start button is pressed and ends when the end button is pressed, endoscopic images are output from the endoscope 12 to the processing apparatus 14 at predetermined time intervals (e.g., intervals of (A) seconds). In playing the former role of the aforementioned two important roles, the processing apparatus 14 appends meta data to the endoscopic images output at predetermined time intervals. The processing apparatus 14 transmits the endoscopic images, to which the metadata is added, to the image management apparatus 20 every time the image is output or collectively when the examination is ended. The metadata at least includes information for identifying the endoscopic image (image ID), information for identifying the patient (patient ID), information for identifying the examination (examination ID), and imaging date information indicating the date of imaging.

Figure 2:
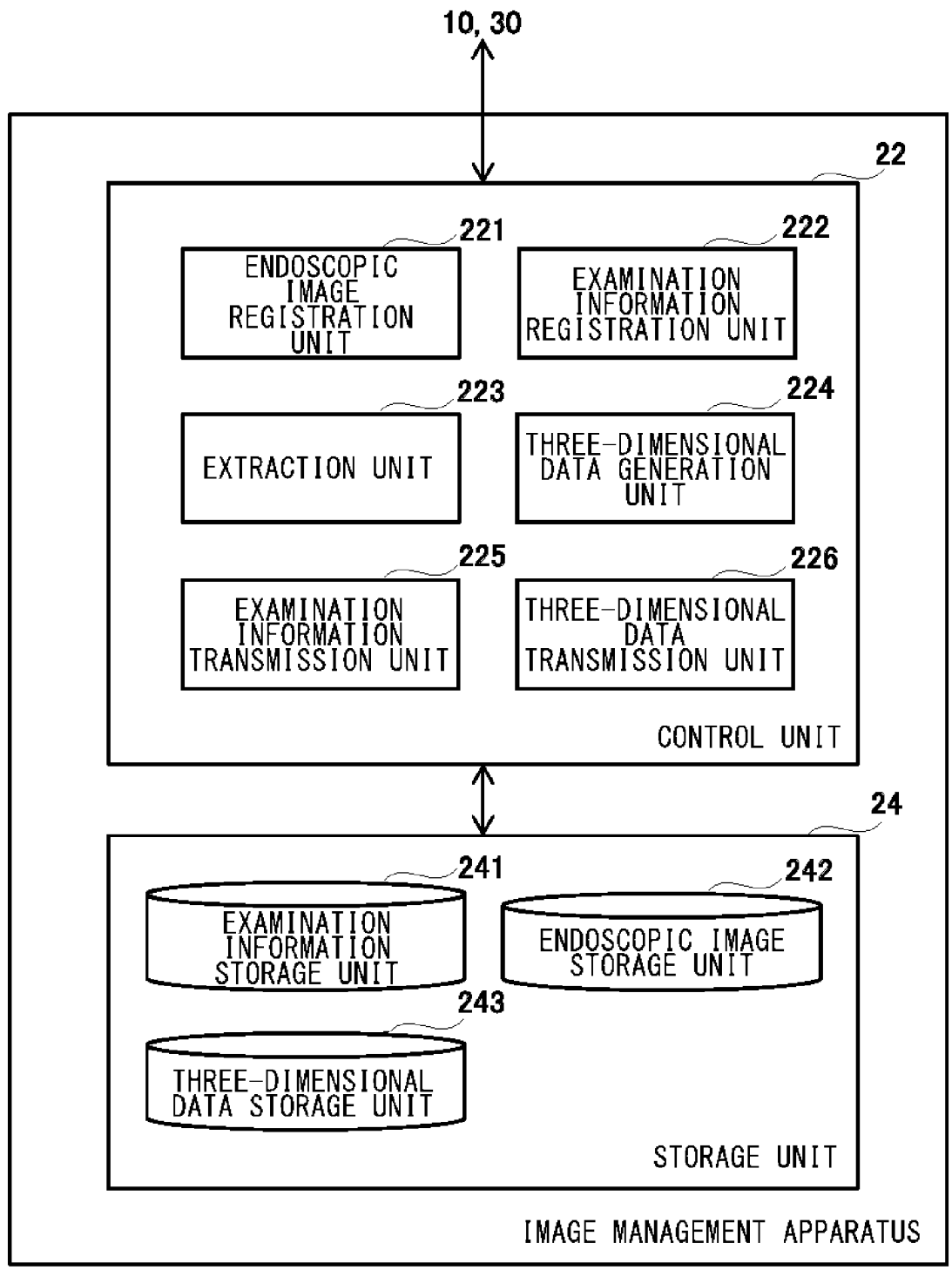
FIG. 2 shows a configuration of the image management apparatus of FIG. 1.

FIG. 2 shows a configuration of the image management apparatus 20. The image management apparatus 20 manages the endoscopic images taken by the endoscope 12. The image management apparatus 20 includes a control unit 22 and a storage 24. The control unit 22 includes an endoscopic image registration unit 221, an examination information registration unit 222, an extraction unit 223, a three-dimensional data generation unit 224, an examination information transmission unit 225, and a three-dimensional data transmission unit 226. The storage 24 includes an examination information storage 241, an endoscopic image storage 242, and a three-dimensional data storage 243.

These functions of the control unit 22 can be implemented by the coordination of hardware resources and software resources, or hardware resources alone. A processor, ROM, RAM, FPGA, and other LSIs can be used as hardware resources. Programs such as operating systems and applications can be used as software resources. The same is true of a control unit 36 described later. The storage 24 is a large-capacity auxiliary storage apparatus and may be comprised of an hard disk drive (HDD) or a flash memory. The same is true of a storage 38 described later.

The endoscopic image storage 242 stores the endoscopic images transmitted from the processing apparatus 14. More specifically, the endoscopic image storage 242 stores all images taken at the predetermined time intervals since the beginning of each examination until the end of the examination. The endoscopic image is stored in association with the image ID and the examination ID.

The three-dimensional data storage 243 stores three-dimensional data generated by the three-dimensional data generation unit 224 as described later.

FIG. 3 shows a data structure in the examination information storage 241. The examination information storage 241 stores examination information. More specifically, the examination information storage 241 stores the examination ID, the patient ID, the examination date, and the image information in association with each other. In the "image information" field, the image ID of the endoscopic image actually taken in each examination is stored. For example, the image IDs "1001-2005" are stored in the examination information with the examination ID "2". This indicates that the endoscopic images having the image IDs "1001-2005" are associated with the examination ID "2", i.e., that the endoscopic images having the image IDs "1001-2005" were acquired in the examination having the examination ID "2". The endoscopic images themselves are stored in the endoscopic image storage 242 as described above.

The endoscopic image registration unit 221 registers the endoscopic image transmitted from the processing apparatus 14 in the endoscopic image storage 242. The endoscopic image registration unit 221 identifies, in particular, the image ID and the examination ID by referring to the metadata for the endoscopic image. The endoscopic image registration unit 221 registers the endoscopic image in the endoscopic image storage 242, associating the endoscopic image with the image ID and the examination ID thus identified.

When the examination start information is transmitted from the endoscopic system 10, the examination information registration unit 222 acquires the examination ID, the patient ID, and the examination date included in the examination start information and registers the set of information in the examination information storage 241. Further, when a new endoscopic image is registered in the endoscopic image storage 242, the examination information registration unit 222 identifies the examination ID by referring to the metadata and links the examination ID with the corresponding examination information. More specifically, the examination information registration unit 222 registers the image ID of the newly registered endoscopic image in the "image information" field of the corresponding examination information.

When the examination end information is transmitted from the endoscopic system 10, the extraction unit 223 acquires the examination ID included in the examination end information and refers to the examination information storage 241 to identify the image IDs of the plurality of endoscopic images linked with the examination ID. The extraction unit 223 extracts the endoscopic images corresponding to the plurality of image IDs thus identified from the endoscopic image storage 242. In other words, the extraction unit 223 extracts all endoscopic images linked with the examination ID, i.e. all endoscopic images acquired in the examination indicated by the examination ID.

The three-dimensional data generation unit 224 generates three-dimensional data indicating the three-dimensional shape of a predetermined part (stomach, small intestine, large intestine) inside the patient's body imaged in the examination, based on the plurality of endoscopic images (two-dimensional images) extracted by the extraction unit 223. For example, the three-dimensional data generation unit 224 may generate three-dimensional data by applying Structure from Motion (SFM) and Multi-view Stereo (MVS) to the plurality of endoscopic images extracted by the extraction unit 223. The three-dimensional data generation unit 224 registers the three-dimensional data thus generated in the three-dimensional data storage 243, associating the three-dimensional data with the examination ID.

The process in the extraction unit 223 and the three-dimensional data generation unit 224 and the examination by the first doctor using the endoscopic system 10 are performed asynchronously.

When the examination information transmission unit 225 acquires a request for display of a list of examination information from the diagnosis supporting apparatus 30 as described later, the examination information transmission unit 225 transmits the examination information stored in the examination information storage 241 to the diagnosis supporting apparatus 30. The examination information thus transmitted includes, for example, the examination ID, the patient ID, and the examination date.

When the three-dimensional data transmission unit 226 receives a request for transmission of three-dimensional data including the examination ID from the diagnosis supporting apparatus 30, the three-dimensional data transmission unit 226 identifies the three-dimensional data corresponding to the examination ID in the three-dimensional data storage 243 and transmits the three-dimensional data thus identified to the diagnosis supporting apparatus 30.

Figure 4:
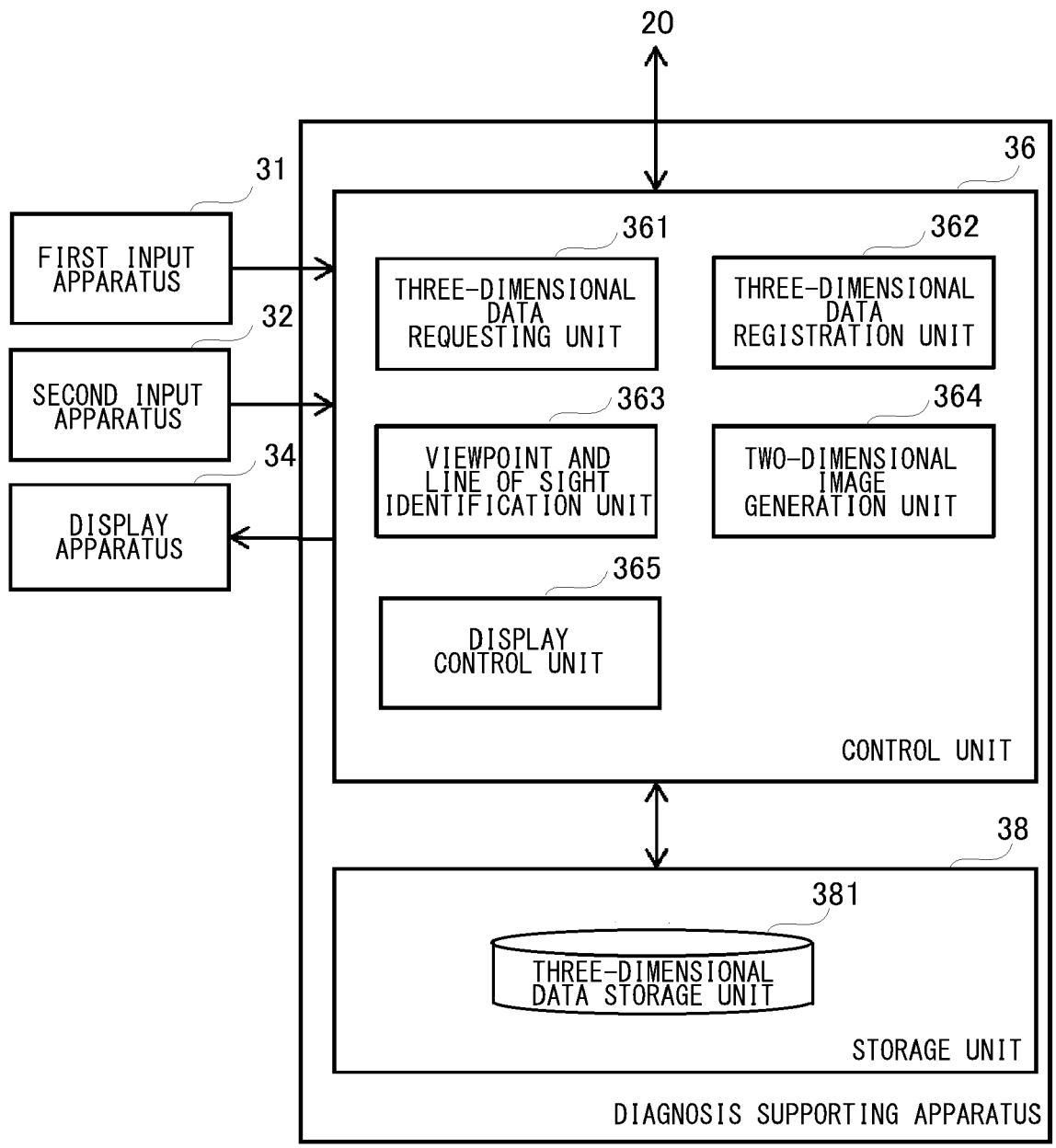
FIG. 4 shows a configuration of the diagnosis supporting apparatus.

FIG. 4 shows a configuration of the diagnosis supporting apparatus 30. The diagnosis supporting apparatus 30 is connected to a first input apparatus 31, a second input apparatus 32, and a display apparatus 34. The first input apparatus is a keyboard or a mouse. The second input apparatus 32 is an input apparatus simulating the user controller 122 of the endoscope 12 and includes an angle knob, a feed switch, and a pull switch. When the feed switch is pressed, the viewpoint position advances into the body as in the case of manual feeding of the inserted part of the actual endoscope by the doctor. When the pull switch is pressed, the viewpoint position moves backward, i.e., toward the insertion opening (e.g., the mouth or the nose) through which the inserted part 121 was inserted as in the case of manual pulling of the inserted part of the actual endoscope by the doctor.

The diagnosis supporting apparatus 30 includes a control unit 36 and a storage 38. The control unit 36 includes a three-dimensional data requesting unit 361, a three-dimensional data registration unit 362, a viewpoint and line of sight identification unit 363, a two-dimensional image generation unit 364, and a display control unit 365. The storage 38 includes a three-dimensional data storage 381. The three-dimensional data storage 381 stores the three-dimensional data in association with the examination ID.

The second doctor enters a request for display of a list of examination information via the first input apparatus 31. The three-dimensional data requesting unit 361 transmits a request for display of a list of examination information to the image management apparatus 20. When the examination information transmission unit 225 in the image management apparatus 20 acquires a request for display of a list of examination information, the examination information transmission unit 225 transmits the examination information stored in the examination information storage 241 to the diagnosis supporting apparatus 30.

FIG. 5 shows an example of a list of examination information. In this example, the information displayed in the list includes the examination ID, the patient ID, and the examination date. The second doctor selects one item of examination information from the list of examination information. The three-dimensional data requesting unit 361 transmits, to the image management apparatus 20, a request for transmission of the three-dimensional data including the examination ID of the selected examination information. When the three-dimensional data transmission unit 226 in the image management apparatus 20 receives a request for transmission of three-dimensional data, the three-dimensional data transmission unit 226 identifies the three-dimensional data corresponding to the examination ID included in the request for transmission and transmits the three-dimensional data thus identified to the diagnosis supporting apparatus 30. The three-dimensional data registration unit 362 acquires the three-dimensional data thus transmitted and registers the acquired three-dimensional data in the three-dimensional data storage 381, associating the three-dimensional data with the examination ID.

The two-dimensional image generation unit 364 generates a two-dimensional image from the three-dimensional data of the selected examination information. The two-dimensional image generation unit 364 generates a two-dimensional image from the three-dimensional data by, for example, perspective projection transform. In particular, the two-dimensional image generation unit 364 generates a two-dimensional image of a predetermined part inside the body indicated by the three-dimensional data as viewed from a viewpoint position designated by the second doctor in the direction of line of sight designated by the second doctor. The display control unit 365 causes the display apparatus 34 to display the two-dimensional image generated by the two-dimensional image generation unit 364.

The viewpoint position and the direction of line of sight of the two-dimensional image initially displayed may be determined by the two-dimensional image generation unit 364. To change the viewpoint position and/or the direction of line of sight of the two-dimensional image displayed, the second doctor manipulates the second input apparatus to effect the change. The viewpoint and line of sight identification unit 363 identifies the viewpoint position and/or the direction of line of sight as changed, based on the manipulation of the second input apparatus 32, and, more specifically, based on the manipulation of the angle knob, the feed switch, or the pull switch. The two-dimensional image generation unit 364 generates a two-dimensional image of a predetermined part inside the body indicated by the three-dimensional data as viewed from the changed viewpoint position identified by the viewpoint and line of sight identification unit 363 in the changed direction of line of sight identified by the viewpoint and line of sight identification unit 363.

A description will now be given of the operation of the endoscopic system 10 configured as described above. The first doctor inserts the inserted part 121 of the endoscope 12 inside the patient's body. The endoscope 12 outputs endoscopic images capturing the inside of the patient's body to the processing apparatus 14 at predetermined time intervals. The processing apparatus 14 transmits the output endoscopic image to the image management apparatus 20. The image management apparatus 20 generates, based on a plurality of endoscopic images for each examination transmitted from the endoscopic system 10, three-dimensional data indicating the three-dimensional shape of a predetermined part inside the body of the patient examined. The diagnosis supporting apparatus 30 transmits a request for transmission of the three-dimensional data designated by the second doctor to the image management apparatus 20. When the image management apparatus 20 acquires the request for transmission, the image management apparatus 20 identifies the three-dimensional data corresponding to the request for transmission and transmits the three-dimensional data to the diagnosis supporting apparatus 30. The diagnosis supporting apparatus 30 generates, from the three-dimensional data transmitted from the image management apparatus 20 based on the request for transmission, a two-dimensional image of a predetermined part inside the body indicated by the three-dimensional data as viewed from the viewpoint position designated by the second doctor in the direction of line of sight designated by the second doctor.

As described above, according to the endoscopic system 10 according to the embodiment, the second doctor can view a predetermined part inside the body as viewed from a desired viewpoint position in a desired direction of sight as in the case of manipulating the endoscope 12 on his or her own to perform an endoscopic examination. This makes it possible to make a highly precise diagnosis.

Second Embodiment

In the first embodiment, a description is given of a case of extracting all endoscopic images acquired in a given examination and generating three-dimensional data corresponding to the examination based on the extracted images. In the second embodiment, some of all of the endoscopic images acquired in a given examination are extracted, and three-dimensional data corresponding to the examination are generated based on the extracted images. Hereinafter, the difference from the first embodiment will be highlighted.

The processing apparatus 14 according to this embodiment further includes, in the metadata appended to the endoscopic image, manipulation information indicating a manipulation of the endoscope 12 performed when the image was taken. The manipulation information at least incudes tip part information indicating the orientation of the tip part 121a. In this example, the tip part information is information on the angle of the angle knob occurring when the image was taken.

In the image management apparatus 20, the endoscopic image registration unit 221 registers the endoscopic image transmitted from the processing apparatus 14 in the endoscopic image storage 242. The endoscopic image registration unit 221 identifies, in particular, the image ID, the examination ID, and the manipulation information by referring to the metadata for the endoscopic image. The endoscopic image registration unit 221 registers the endoscopic image in the endoscopic image storage 242, associating the endoscopic image with the image ID, the examination ID, and the manipulation information thus identified.

Figure 6:
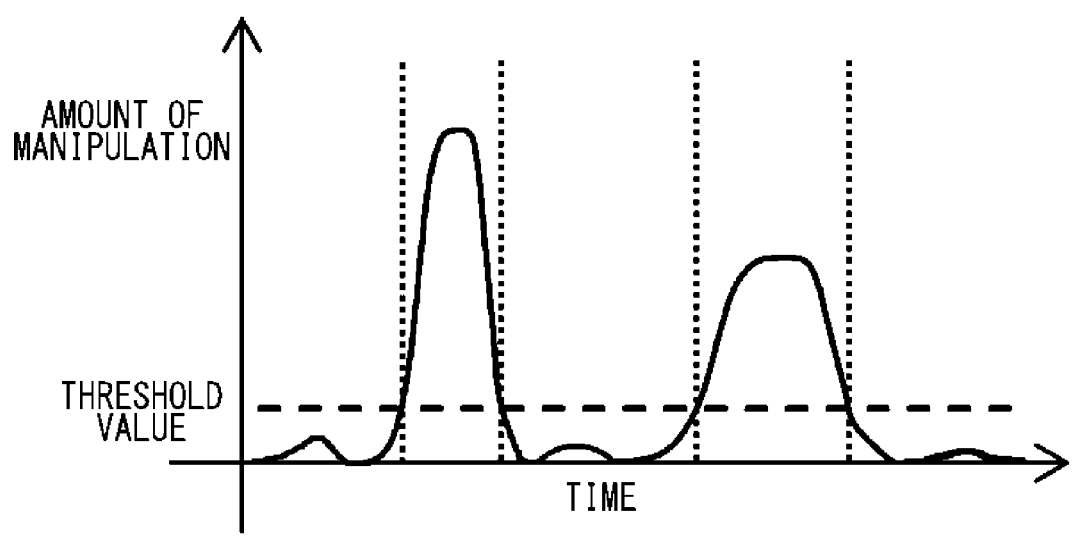
FIG. 6 shows extraction of an endoscopic image by the extraction unit.

FIG. 6 shows extraction of an endoscopic image by the extraction unit 223. In this embodiment, as in the first embodiment, the extraction unit 223 first identifies the image IDs of the plurality of endoscopic images linked with the examination ID. Of the endoscopic images with the image IDs thus identified, the extraction unit 223 extracts endoscopic images taken during a period of time in which the amount of manipulation of the endoscope 12 is great, i.e., a period of time in which the amount of manipulation is equal to or greater than a predetermined threshold value. The amount of manipulation is determined by the manipulation information. The amount of manipulation may be an amount of manipulation of the tip part of the endoscope 12. In this case, the amount of manipulation is an absolute value of the change in the angle of the angle knob per a unit time and is calculated from the tip part information (information on the angle of the angle knob) included in the manipulation information of each endoscopic image and from the interval of acquiring endoscopic images. In the example of FIG. 6, the amounts of manipulation in two periods of time are equal to or greater than the threshold value so that the endoscopic images in these periods of time are extracted. The extraction unit 223 can be said to exclude, from the endoscopic images extracted based on the examination ID, those endoscopic images of periods of time in which the amount of manipulation is not so great, i.e., periods of time in which the amount of manipulation is less than the threshold value.

When the first doctor focuses on a region in the body for diagnosis of a pathological abnormality, for example, the amount of manipulation of the endoscope 12 by the first doctor will increase as the doctor attempts to view the region at a position and an angle that make it easy to view the region. In other words, the endoscopic image taken during a period of time in which the amount of manipulation is great is likely to be an endoscopic image capturing the region focused by the first doctor (hereinafter, also referred to as "region of interest"). Meanwhile, the endoscopic image taken during a period of time in which the amount of manipulation is not so great is less likely to be an endoscopic image capturing a region of interest.

Thus, according to this embodiment, the extraction unit 223 can extract endoscopic images that are likely to be endoscopic images capturing a region of interest, as endoscopic images for generating three-dimensional data. Meanwhile, the extraction unit 223 can exclude endoscopic images that are less likely to be endoscopic images capturing a region of interest, from endoscopic images for generating three-dimensional data. In other words, according to this embodiment, endoscopic images capturing a region of interest can be extracted as endoscopic images for generating three-dimensional data, and the number of endoscopic images used for generation can be reduced at the same time. This reduces the processing time in the three-dimensional data generation unit 224. Also, the volume of the three-dimensional data is reduced, and the area for saving the data can be reduced.

In a variation, the extraction unit 223 may extract endoscopic images taken during a period of time in which the amount of manipulation is equal to or greater than a threshold value and during a neighboring period of time. The neighboring period of time may be a predetermined period of time subsequent to the period of time in which the amount of manipulation is equal to or greater than the threshold value. When the endoscope 12 is adjusted to the position and angle at which the region of interest is easily viewed, the first doctor is expected to stop the endoscope 12 at that position and angle and view the region of interest. Therefore, it is likely that endoscopic images taken during the subsequent predetermined period of time in which the amount of manipulation is not so great include endoscopic images that capture the region of interest. Thus, by also extracting endoscopic images taken during the subsequent predetermined period of time, it is further ensured that endoscopic images capturing the region of interest are included in endoscopic images for generating three-dimensional data.

The neighboring period may include both a predetermined period of time preceding and a predetermined period of time subsequent to the period of time in which the amount of manipulation is equal to or greater than the threshold value. In this way, it is further ensured that endoscopic images capturing the region of interest are included in endoscopic images for generating three-dimensional data. As described above, it is likely that endoscopic images taken during the subsequent predetermined period of time include endoscopic images that capture the region of interest. Therefore, the subsequent predetermined period of time may be configured to be longer than the preceding predetermined period of time.

Third Embodiment

In the third embodiment, a description will be given of a method of increasing the speed of the process by the three-dimensional data generation unit 224 in the image management apparatus 20. The following description highlights a difference from the first embodiment.

As in the second embodiment, the processing apparatus 14 further includes, in the metadata appended to the endoscopic image, manipulation information at least including tip part information.

In the image management apparatus 20, the endoscopic image registration unit 221 identifies the image ID, the examination ID, and the manipulation information by referring to the metadata for the endoscopic image. The endoscopic image registration unit 221 registers the endoscopic image in the endoscopic image storage 242, associating the endoscopic image with the image ID, the examination ID, and the manipulation information thus identified. In this embodiment, the endoscopic image registration unit 221 does not register, in the tip part information in the manipulation information in the endoscopic image storage 242, angle information on the angle knob itself. Instead, the endoscopic image registration unit 221 registers angle information derived from coding the angle into one of a forward direction (not less than 0° and less than 60°), a transversal direction (not less than 60° and less than 120°), and a reverse direction (not less than 120° and not more than) 180°.

In generating three-dimensional data from two-dimensional endoscopic images, the three-dimensional data generation unit 224 searches for a feature point in each endoscopic image extracted by the extraction unit 223 for which a correspondence between that endoscopic image and a further endoscopic image extracted is identified, although the feature was not discussed in detail in the first embodiment. If all of the other endoscopic images extracted are subject to the search in this process, the searching process by the three-dimensional data generation unit 224 takes a long time.

This is addressed in this embodiment by searching, of the other endoscopic images, only those endoscopic images that are likely to include a corresponding feature point. A specific description will be given with reference to FIGS. 7A, 7B, and 7C. In the following description, it is assumed that the inserted part 121 of the endoscope 12 is inserted all the way into the body before the examination is started, and the doctor views the image in the examination while pulling the inserted part 121.

Figure 7A:
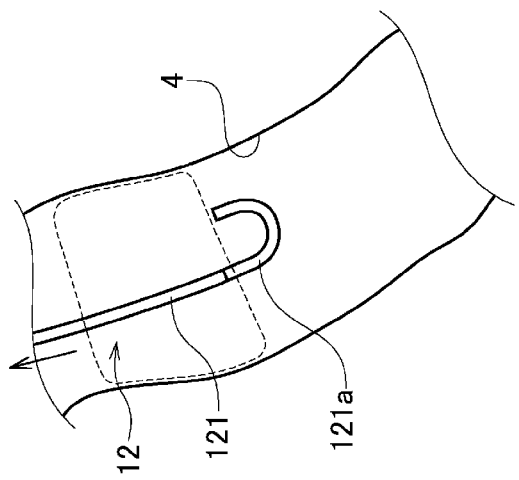
FIGS. 7A, 7B, and 7C show how the tip part of the endoscope is oriented during an examination.
Figure 7B:
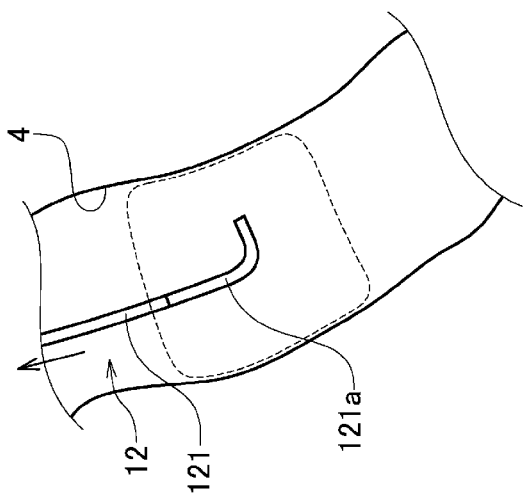
Figure 7C:
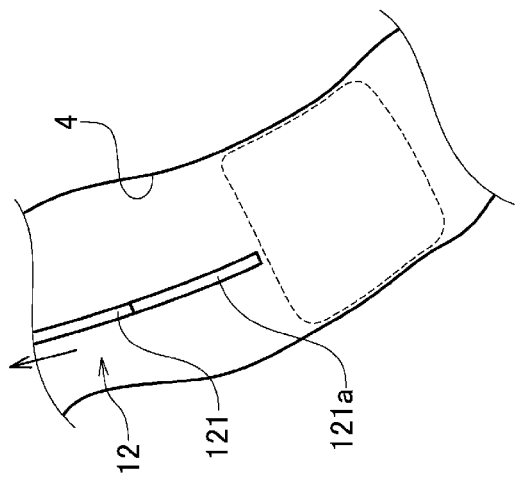

FIGS. 7A, 7B, and 7C show how the tip part 121a of the endoscope is oriented during an examination. In FIGS. 7A, 7B, and 7C, the arrow indicates an orientation in which the inserted part 121 is pulled. FIG. 7A shows how the tip part 121a is oriented when the angle knob is manipulated in a forward direction (e.g., at an angle of 0°), FIG. 7B shows how the tip part 121a is oriented when the angle knob is manipulated in a transversal direction (e.g., at an angle of) 90°, and FIG. 7C shows how the tip part 121a is oriented when the angle knob is manipulated in a reverse direction (e.g., at an angle of 180°).

When the tip part information on the endoscopic image subject to a search indicates a forward direction, the endoscopic image subject to the search is considered to be an endoscopic image taken when the tip part 121a is in a state as shown in FIG. 7A, i.e., an endoscopic image capturing the side toward the depth of the body. Therefore, considering the fact that the image is viewed while the inserted part 121 is being pulled, it is considered to be likely that endoscopic images taken before the endoscopic image subject to the search, and, more specifically, endoscopic images taken when the tip part 121a was in a range encircled by the dotted line in FIG. 7A, include a feature point corresponding to the endoscopic image subject to a search. In this case, therefore, the three-dimensional data generation unit 224 searches endoscopic images taken before the endoscopic image subject to the search for a feature point or searches endoscopic images taken during a predetermined period of time before the endoscopic image subject to the search for a feature point.

When the tip part information on the endoscopic image subject to the search indicates a transversal direction, the endoscopic image subject to the search is considered to be an endoscopic image taken when the tip part 121a is in a state as shown in FIG. 7B, i.e., an endoscopic image capturing a wall face 4 of an internal organ. Therefore, it is considered to be likely that endoscopic images taken before and after the endoscopic image subject to the search, and, more specifically, endoscopic images taken when the tip part 121a was in a range encircled by the dotted line in FIG. 7B, include a feature point corresponding to the endoscopic image subject to the search. In this case, therefore, the three-dimensional data generation unit 224 searches endoscopic images taken during a predetermined period of time before and after the endoscopic image subject to the search for a feature point.

When the tip part information on the endoscopic image subject to the search indicates a reverse direction, the endoscopic image subject to the search is considered to be an endoscopic image taken when the tip part 121a is in a state as shown in FIG. 7C, i.e., an endoscopic image capturing the insertion opening of the inserted part 121. Therefore, considering the fact that the image is viewed while the inserted part 121 is being pulled, it is considered to be likely that endoscopic images taken after the endoscopic image subject to the search, and, more specifically, endoscopic images taken when the tip part 121a was in a range encircled by the dotted line in FIG. 7c, include a feature point corresponding to the endoscopic image subject to the search. In this case, therefore, the three-dimensional data generation unit 224 searches endoscopic images taken after the endoscopic image subject to the search for a feature point or searches endoscopic images taken during a predetermined period of time after the endoscopic image subject to the search for a feature point.

According to this embodiment, the three-dimensional data generation unit 224 searches only those endoscopic images that are likely to include a feature point corresponding to each of the endoscopic images extracted. Accordingly, the processing time is reduced.

In a variation to the third embodiment, the three-dimensional data generation unit 224 may search endoscopic images having the same tip part information as the endoscopic image subject to the search for a feature point. According to this variation, the same advantage as provided by the third embodiment can be provided.

Fourth Embodiment

In the fourth embodiment, a description will be given of a method of reducing the network load between the image management apparatus 20 and the diagnosis supporting apparatus 30. The following description highlights a difference from the first embodiment.

In the diagnosis supporting apparatus 30, the three-dimensional data requesting unit 361 requests three-dimensional data determined by the manipulation by the second doctor. Specifically, assuming that the image is viewed in the examination while the inserted part 121 is being pulled as in the third embodiment, the three-dimensional data requesting unit 361 requests three-dimensional data in a predetermined range more toward the depth of the body than the current viewpoint position, when the second doctor manipulates the angle knob of the second input apparatus 32 to an angle not less than 0° and less than 60° (i.e., in a forward direction). When the second doctor manipulates the angle knob to an angle not less than 60° and less than 120° (i.e., in a transversal direction), the three-dimensional data requesting unit 361 requests a portion of the three-dimensional data in a predetermined range more toward the depth of the body and more toward the insertion opening than the current viewpoint position. When the second doctor manipulates the angle knob to an angle not less than 120° and not more than 180° (i.e., in a reverse direction), the three-dimensional data requesting unit 361 requests a portion of the three-dimensional data in a predetermined range more toward the insertion opening than the current viewpoint position.

In the image management apparatus 20, the three-dimensional data transmission unit 226 extracts a portion determined by the manipulation by the second doctor from the three-dimensional data corresponding to the transmission request and transmits the extracted data to the diagnosis supporting apparatus 30.

According to this embodiment, the volume of three-dimensional data transmitted from the image management apparatus 20 to the diagnosis supporting apparatus 30 is relatively smaller so that the network load between the image management apparatus 20 and the diagnosis supporting apparatus 30 is reduced.

Sixth Embodiment

In the fifth embodiment, a description will be given of a case of generating a plurality of sets of three-dimensional data based on endoscopic images acquired in a single examination.

As in the second embodiment, the processing apparatus 14 further includes, in the metadata appended to the endoscopic image, manipulation information at least including tip part information. The tip information may be the angle information itself on the angle knob or angle information derived from coding the angle into one of a forward direction (not less than 0° and less than 60°), a transversal direction (not less than 60° and less than 120°), and a reverse direction (not less than 120° and not more than) 180°.

Figure 8:
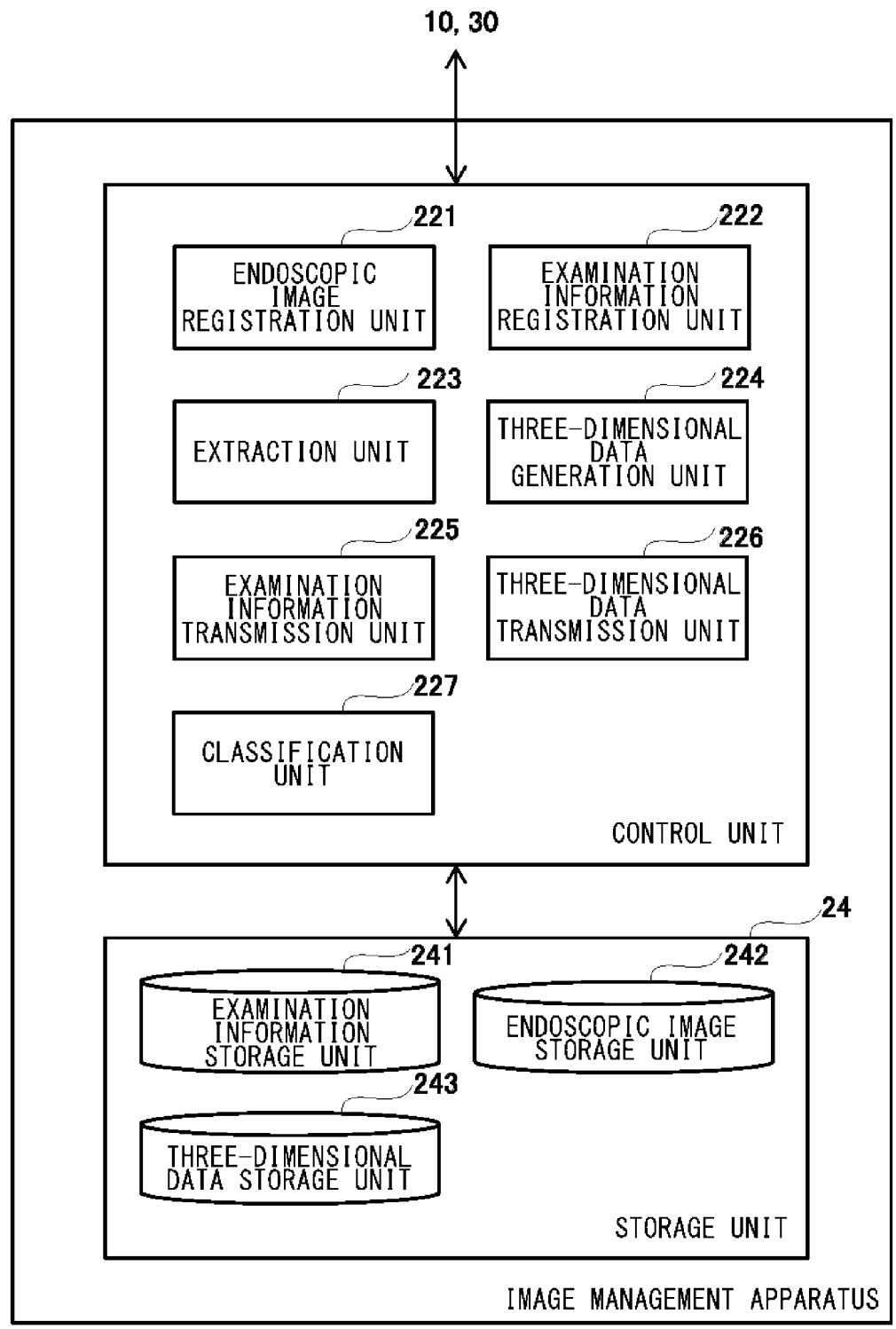
FIG. 8 shows a configuration of the image management apparatus of the endoscopic task supporting system according to the fifth embodiment.

FIG. 8 shows a configuration of the image management apparatus 20. In this embodiment, the control unit 22 further includes a classification unit 227.

The endoscopic image registration unit 221 identifies the image ID, the examination ID, and the manipulation information by referring to the metadata for the endoscopic image. The endoscopic image registration unit 221 registers the endoscopic image in the endoscopic image storage 242, associating the endoscopic image with the image ID, the examination ID, and the manipulation information thus identified.

The classification unit 227 classifies the plurality of endoscopic images extracted by the extraction unit 223 into a plurality of groups, based on the tip part information included in the manipulation information associated with the respective endoscopic images. In this case, the classification unit 227 classifies the plurality of endoscopic images into three groups, i.e., a group in which the tip part information indicates a forward direction, a group in which the tip part information indicates a transversal direction, and a group in which the tip part information indicates a reverse direction.

The three-dimensional data generation unit 224 generates three-dimensional data for each group organized by the classification unit 227. The three-dimensional data generation unit 224 generates three-dimensional data based on the plurality of endoscopic images included in the group of a forward direction (hereinafter, referred to as forward-direction three-dimensional data), three-dimensional data based on the plurality of endoscopic images included in the group of a transversal direction (hereinafter, referred to as transversal-direction three-dimensional data), and three-dimensional data based on the plurality of endoscopic images included in the group of a reverse direction (hereinafter, referred to as reverse-direction three-dimensional data).

In the diagnosis supporting apparatus 30, the three-dimensional data requesting unit 361 requests, of the three-dimensional data of the respective groups, three-dimensional data determined by the manipulation by the second doctor. More specifically, the three-dimensional data requesting unit 361 requests the three-dimensional data of the group of a forward direction when the second doctor manipulates the angle knob of the second input apparatus 32 to an angle not less than 0° and less than 60°, requests the three-dimensional data of group of a transversal direction when the second doctor manipulates the angle knob to an angle not less than 60° and less than 120°, and requests the three-dimensional data of the group of a reverse direction when the second doctor manipulates the angle knob to an angle not less than 120° and not more than 180°. Further, the three-dimensional data requesting unit 361 acquires the transmitted three-dimensional data and stores the acquired three-dimensional data in the three-dimensional data storage 381, associating the three-dimensional data with the examination ID and the group (forward direction, transversal direction, and reverse direction) of the three-dimensional data.

The two-dimensional image generation unit 364 generates a two-dimensional image from the forward-direction three-dimensional data, the transversal-direction three-dimensional data, or the reverse-direction three-dimensional data. When the second doctor manipulates the angle knob of the second input apparatus 32 to an angle not less than 0° and less than 60° (i.e., in a forward direction), for example, the two-dimensional image generation unit 364 generates two-dimensional image from the forward-direction three-dimensional data. In this case, if the forward-direction three-dimensional data is already stored in the three-dimensional data storage 381, the two-dimensional image generation unit 364 generates two-dimensional data from the forward-direction three-dimensional data. If the forward-direction three-dimensional data is not stored in the three-dimensional data storage 381, the three-dimensional data requesting unit 361 acquires the forward-direction three-dimensional data and registers the acquired data in the three-dimensional data storage 381 as described above prior to the process by the two-dimensional image generation unit 364.

As in the first embodiment, the viewpoint position and the direction of line of sight of the two-dimensional image initially displayed may be determined by the two-dimensional image generation unit 364. For example, a two dimensional image showing the farthest end in the forward direction (e.g., in the direction of the angle of 0°) may be generated. In this case, the three-dimensional data requesting unit 361 requests and acquires the forward-direction three-dimensional data before the two-dimensional image generation unit 364 generates the two-dimensional image initially displayed.

According to this embodiment, the two-dimensional image is generated from the three-dimensional data corresponding to the angle of the angle knob. Therefore, the two-dimensional image of an image quality closer to that of the endoscopic image actually taken by the endoscope 12 can be generated than otherwise.

Generation of three-dimensional data by the three-dimensional data generation unit 224 includes restoration of the three-dimensional shape and texture mapping. In a variation, the three-dimensional data generation unit 224 generating three-dimensional data for a given group may use all endoscopic images extracted by the extraction unit 223 for restoration of the three-dimensional shape and use a plurality of endoscopic images included in that group for texture mapping. For example, the three-dimensional data generation unit 224 generating the forward-direction three-dimensional data may use all endoscopic images extracted by the extraction unit 223 for restoration of the three-dimensional shape and use a plurality of endoscopic images included in the group of a forward direction. In an observation using the endoscope 12, the brightness or color of a given region may differ depending on the direction of view, due to various factors such as how the region is illuminated. According to this variation, the two-dimensional image generation unit 364 can generate a two-dimensional image of the brightness or color similar to that of the case of observing the region by using the endoscope 12.

Described above is an explanation of the present invention based on an exemplary embodiment. The embodiment is intended to be illustrative only and it will be understood by those skilled in the art that various modifications to combinations of constituting elements and processes are possible and that such modifications are also within the scope of the present invention.

In the first through fifth embodiments, the diagnosis supporting apparatus 30 is described as being provided with the two-dimensional image generation unit 364. Alternatively, the image management apparatus 20 may be provided with the function of the two-dimensional image generation unit. In this case, the viewpoint and line of sight identification unit 363 having identified the changed viewpoint position and/or the direction of line of sight, transmits the position and/or the direction to the image management apparatus 20.

The processing apparatus 14 may include, in the metadata for the endoscopic image designated by the first doctor, designation information indicating the designation, although the feature is not referred to in the first through fifth embodiments and the aforementioned variation. Designation by the first doctor may be made by allowing the doctor to perform a certain manipulation in the user controller 122 when the endoscope 12 images a region of interest. Further, the first doctor may acquire an endoscopic image for attachment to a report of the examination findings. For example, the user controller 122 may include a release switch, and the endoscopic image is acquired as the first doctor presses the release switch. Designation by the first doctor may be made in a manipulation for acquiring an endoscopic image, i.e. by pressing the release switch.

In the image management apparatus 20, the extraction unit 223 may extract a plurality of endoscopic images including an endoscopic image to which designation information is appended. For example, the extraction unit 223 may extract an endoscopic image to which designation information is appended and endoscopic images taken during a predetermined period of time before and after.

In the first through fifth embodiments and the variation described above, the endoscope 12 is described as being a medical endoscope for imaging the inside of the patient's body, and the endoscopic image is described as being an image capturing the inside of the patient's body. However, application of the disclosure is not limited to these examples. For example, the technical idea of the embodiments can be applied to a case in which the endoscope 12 is an industrial endoscope, and the endoscopic images capture the inside of a pipe, machine, structure, etc. In other words, the nature of the target subject to observation captured by the endoscopic image does not matter.

What is claimed is:

1. An endoscopic task supporting system comprising:
   an endoscopic system that is manipulated by a first manipulator, the endoscopic system comprising an endoscope configured to acquire a plurality of endoscopic images in a chronological order;
   an image management apparatus that includes an image storage that stores the plurality of endoscopic images acquired by the endoscopic system in a chronological order and a first processor comprising hardware, wherein the first processor is configured to generate three-dimensional data indicating a three-dimensional shape of a predetermined part subject to observation, based on the plurality of endoscopic images stored in the image storage;

an input device manipulated by a second manipulator different from the first manipulator; and a diagnosis supporting apparatus that includes a second processor comprising hardware, wherein the second processor is configured to generate, from the generated three-dimensional data, a two-dimensional image corresponding to a viewpoint position and a direction of line of sight entered in the input device, and cause a predetermined display unit to display the generated two-dimensional image;

wherein the image storage stores each of the plurality of endoscopic images, associating each endoscopic image of the plurality of endoscopic images with manipulation information indicating a manipulation of the endoscope performed when each endoscopic image is taken;

the first processor is configured to:
- extract endoscopic images from the plurality of endoscopic images stored in the image storage, based on the manipulation information;
- generate three-dimensional data based on the extracted endoscopic images; and
- identify an amount of manipulation of a tip part of the endoscope, based on the manipulation information, and extract, from the plurality of endoscopic images stored in the image storage, endoscopic images taken during a period of time in which the amount of manipulation is greater than a predetermined threshold value or during a period of time in which the amount of manipulation is greater than the predetermined threshold value and during a neighboring period of time.

2. The endoscopic task supporting system according to claim 1, wherein the first processor is configured to:
- classify the plurality of endoscopic images stored in the image storage into a plurality of groups, based on the amount of manipulation of the tip part; and
- generate three-dimensional data for each group.

3. The endoscopic task supporting system according to claim 2, wherein
- the second processor is configured to generate a two-dimensional image from the three-dimensional data of a plurality of sets of generated three-dimensional data based on a group of the plurality of groups corresponding to the direction of line of sight entered.

4. An endoscopic task supporting method for execution by an image processing system capable of accessing a predetermined storage area that stores a plurality of endoscopic images acquired in a chronological order, the method comprising:

causing the storage area to store a plurality of endoscopic images acquired as a first manipulator manipulates an endoscopic system comprising an endoscope configured to acquire the plurality of endoscopic images, wherein the storage area stores each of the plurality of endoscopic images, associating each endoscopic image of the plurality of endoscopic images with manipulation information indicating a manipulation of the endoscope performed when each endoscopic image is taken;

generating three-dimensional data indicating a three-dimensional shape of a predetermined part inside a body, based on the plurality of endoscopic images stored in the storage area;

generating, from the three-dimensional data generated, a two-dimensional image corresponding to a viewpoint position and a direction of line of sight entered as a second manipulator different from the first manipulator manipulates an input device;

causing a predetermined display unit to display the two-dimensional image generated;

extracting endoscopic images from the plurality of endoscopic images stored in the image storage, based on the manipulation information;

generating three-dimensional data based on the extracted endoscopic images; and identifying an amount of manipulation of a tip part of the endoscope, based on the manipulation information, and extracting, from the plurality of endoscopic images stored in the image storage, endoscopic images taken during a period of time in which the amount of manipulation is greater than a predetermined threshold value or during a period of time in which the amount of manipulation is greater than the predetermined threshold value and during a neighboring period of time.

5. A program embedded in a non-transitory computer readable recording medium and causing an endoscopic system comprising an endoscope, and capable of accessing a predetermined storage area that stores a plurality of endoscopic images acquired by the endoscope in a time series to embody modules comprising:

a module that causes the storage area to store a plurality of endoscopic images acquired as a first manipulator manipulates an endoscopic system, wherein the storage area stores each of the plurality of endoscopic images, associating each endoscopic image of the plurality of endoscopic images with manipulation information indicating a manipulation of the endoscope performed when each endoscopic image is taken;

a module that generates three-dimensional data indicating a three-dimensional shape of a predetermined part inside a body, based on the plurality of endoscopic images stored in the storage area;

a module that generates, from the three-dimensional data generated, a two-dimensional image corresponding to a viewpoint position and a direction of line of sight entered as a second manipulator different from the first manipulator manipulates an input device;

a module that causes a predetermined display unit to display the two-dimensional image generated;

a module that extracts endoscopic images from the plurality of endoscopic images stored in the image storage, based on the manipulation information;

a module that generates three-dimensional data based on the extracted endoscopic images; and a module that identifies an amount of manipulation of a tip part of the endoscope, based on the manipulation information, and extracts, from the plurality of endoscopic images stored in the image storage, endoscopic images taken during a period of time in which the amount of manipulation is greater than a predetermined threshold value or during a period of time in which the amount of manipulation is greater than the predetermined threshold value and during a neighboring period of time.

* * * * *